United States Patent
Hiltunen et al.

(10) Patent No.: US 11,326,199 B2
(45) Date of Patent: May 10, 2022

(54) AFFINITY MEDIATED TRANSPORT AMPLIFICATION

(71) Applicant: TEKNOLOGIAN TUTKIMUSKESKUS VTT OY, Espoo (FI)

(72) Inventors: Jussi Hiltunen, Oulu (FI); Prateek Singh, Oulu (FI)

(73) Assignee: TEKNOLOGIAN TUTKIMUSKESKUS VTT OY, Espoo (FI)

( * ) Notice: Subject to any disclaimer, the term of this patent is extended or adjusted under 35 U.S.C. 154(b) by 0 days.

(21) Appl. No.: 17/338,922

(22) Filed: Jun. 4, 2021

(65) Prior Publication Data

US 2021/0292808 A1 Sep. 23, 2021

Related U.S. Application Data

(63) Continuation of application No. PCT/FI2019/050810, filed on Nov. 14, 2019.

(30) Foreign Application Priority Data

Dec. 5, 2018 (FI) ...................................... 20186055

(51) Int. Cl.
*C12Q 1/6804* (2018.01)
*B01L 3/00* (2006.01)

(52) U.S. Cl.
CPC ...... *C12Q 1/6804* (2013.01); *B01L 3/502715* (2013.01); *B01L 2400/043* (2013.01)

(58) Field of Classification Search
CPC ............. C12Q 1/6804; B01L 3/502715; B01L 2400/043; B01L 3/502761; B01L 3/5027; G01N 33/54353; G01N 33/54333; G01N 33/54313; G01N 35/0098
See application file for complete search history.

(56) References Cited

U.S. PATENT DOCUMENTS

| 2008/0038810 A1* | 2/2008 | Pollack ............. B01L 3/502784 435/283.1 |
| 2013/0217584 A1 | 8/2013 | Zhang et al. |
| 2014/0193807 A1 | 7/2014 | Pamula et al. |
| 2017/0131269 A1 | 5/2017 | Peretz |

FOREIGN PATENT DOCUMENTS

| EP | 2014761 B1 | 9/2016 |
| WO | 2007110779 A2 | 10/2007 |
| WO | 2011050226 A1 | 4/2011 |
| WO | 2012016357 A1 | 2/2012 |
| WO | 2016175708 A1 | 11/2016 |

OTHER PUBLICATIONS

International Search Report issued by the European Patent Office acting as the International Searching Authority in relation to International Application No. PCT/FI2019/050810 dated Feb. 3, 2020 (3 pages).
Written Opinion of the International Searching Authority issued by the European Patent Office acting as the International Searching Authority in relation to International Application No. PCT/FI2019/050810 dated Feb. 3, 2020 (5 pages).
Decision—Application Accepted issued by the Finnish Patent and Registration Office in relation to Finnish Application No. 20186055 dated May 29, 2020 (1 page).
Communication of Acceptance issued by the Finnish Patent and Registration Office in relation to Finnish Application No. 20186055 dated Feb. 26, 2020 (2 pages).
Office Action issued by the Finnish Patent and Registration Office in relation to Finnish Application No. 20186055 dated Jun. 19, 2019 (7 pages).
Finnish Search Report issued by the Finnish Patent and Registration Office in relation to Finnish Application No. 20186055 dated Jun. 19, 2019 (2 pages).
Mao, X. et al. Cyclic accumulation of nanoparticles: A new strategy for electrochemical immunoassay based on the reversible reaction between dethiobiotin and avidin. Analytica Chimica Acta, Jan. 2006, vol. 557, No. 1-2, pp. 159-163 <DOI:10.1016/j.aca.2005.09.078> abstract; figure 3.
Kemper, D. W. M et al. Analytical evaluation of a new point of care system for measuring cardiac Troponin I. Clinical Biochemistry, Mar. 2017, vol. 50, No. 4-5, pp. 174-180 <DOI10.1016/j.clinbiochem.2016.11.011> p. 175, section 2.2. Design of the minicare cTnl assay; figure 1.
Immuno-PCR: An ultr sensitive immunoassay for biomolecular detection. Anal Chim Acta. Mar. 3, 2016;910:12-24.
Proximity ligation assays for sensitive and specific protein analyses. Analytical Biochemistry. 345 (1): 2-9, Feb. 2005.
Magnetic separation techniques in diagnostic microbiology. Clinical Microbiology Reviews, Jan. 1994, p. 43-54.
Official Finnish Letters Patent No. FI128458 B issued May 29, 2020 in relation to Finnish Application No. 20186055 (22 pages).

* cited by examiner

*Primary Examiner* — Cynthia B Wilder
(74) *Attorney, Agent, or Firm* — Robert P. Michal, Esq.; Carter, DeLuca & Farrell LLP

(57) ABSTRACT

A method for amplification in a microfluidic assay, includes binding an analyte to a transport element, wherein the transport element includes a particle and a first antibody element and the analyte is bound to the first antibody element; moving the transport element with the analyte towards a tracer storage site including tracer elements which includes a first binder element, a label element and a second antibody element; binding the analyte to the second antibody element; moving the transport element with the analyte and the tracer element towards a tracer transport site including second binder elements; binding the first binder element with a second binder element; moving the transport element with the analyte towards the tracer storage site so that the analyte is detached from the second antibody element of the tracer element while the first binder element remains bound to the second binder element.

11 Claims, 3 Drawing Sheets

AFFINITY MEDIATED TRANSPORT AMPLIFICATION

CROSS-REFERENCE TO RELATED APPLICATIONS

This application is a continuation of PCT International Application No. PCT/FI2019/050810 filed Nov. 14, 2019, which claims priority to Finnish Patent Application No. 20186055, filed Dec. 5, 2018, the disclosure of each of these applications is expressly incorporated herein by reference in their entirety.

TECHNICAL FIELD

The present application generally relates to analyte detection. In particular, but not exclusively, the present application relates to analyte detection using antibodies. In particular, but not exclusively, the present application relates to an amplification protocol in analyte detection.

BACKGROUND

This section illustrates useful background information without admission of any technique described herein being representative of the state of the art.

Detection of analytes, for example using an immunoassay, with increased sensitivity is increasingly important in many applications, for example in the field of biotechnology and medicine. The desired sensitivity is for detection of even single molecules in a complex mixture. However, currently such desired sensitivity needs to rely on signal amplification since a small amount of molecules or particles, let alone a single molecule, is usually unable to generate a strong enough signal otherwise.

Currently direct amplification protocols do not exist for most analytes, such as proteins. The existing methods rely on the amplification of the immuno-binding product in an equilibrium state, such as enzymatic amplification. For example, in immuno-PCR, antigen bound DNA is subsequently amplified by polymerase-chain-reaction (PCR). Another known example is proximity ligation assay (PLA), where also DNA-sequences are also primarily bound with target molecule (protein) and the signal is subsequently amplified with known amplification protocols. As a further example, immunomagnetic separation is previously known to concentrate analyte molecules.

Such previously known methods have been described for example in publications: "Immuno-PCR: An ultrasensitive immunoassay for biomolecular detection.". Anal Chim Acta. 2016 Mar. 3; 910:12-24; "Proximity ligation assays for sensitive and specific protein analyses". Analytical Biochemistry. 345 (1): 2-9; and "Magnetic separation techniques in diagnostic microbiology". CLINICAL MICROBIOLOGY REVIEWS, January 1994, p. 43-54. Furthermore, previous published patent applications WO201150226 and US20130217584 relate to known amplification methods.

However, in existing methods, only a single binding cycle takes place. It is the object of the current invention to provide an amplification protocol mitigating the problems of the prior art and increasing sensitivity by multiplying the number of binding events by utilizing affinity mediated transport amplification.

SUMMARY

Various aspects of examples of the invention are set out in the claims.

According to a first example aspect of the present invention, there is provided a method for amplification in a microfluidic assay, comprising
    binding an analyte to a transport element, wherein the transport element comprises a particle and a first antibody element and the analyte is bound to the first antibody element;
    moving the transport element with the analyte bound thereto towards a tracer storage site comprising tracer elements, wherein a tracer element comprises a first binder element, a label element and a second antibody element;
    binding the analyte to the second antibody element;
    moving the transport element with the analyte and the tracer element bound therewith towards a tracer transport site comprising second binder elements; binding the first binder element with a second binder element;
    moving the transport element with the analyte bound thereto towards the tracer storage site so that the analyte is detached from the second antibody element of the tracer element while the first binder element remains bound to the second binder element; and
    repeating the steps subsequent to binding the analyte to the transport element a predetermined number of times; wherein
    the first antibody element has a higher affinity for the analyte than the second antibody element.

Moving the transport element may comprise causing a force that moves the transport element.

Moving the transport element may comprise causing a magnetic force and the particles of the transport element may comprise magnetic nanoparticles.

The first binder element may comprise biotin and the second binder element may comprise avidin.

The label element may comprise a fluorescent dye.

According to a second example aspect of the present invention, there is provided a method for detecting an analyte in a microfluidic assay, comprising
    introducing a fluid comprising the analyte to be detected into the assay;
    carrying out the amplification method of any preceding claims; and
    subsequently reading out the result of the assay.

Reading out the result of the assay may comprise fluorescent excitation and optical detection of the resulting fluorescence.

According to a third example aspect of the present invention, there is provided an apparatus for a microfluidic assay, comprising
    a microfluidic chip, comprising at least one input port for introducing a fluid containing an analyte, and at least one assay site, the assay site comprising transport elements, a tracer transport site and a tracer storage site; wherein
    a transport element comprises a particle and a first antibody element and the analyte is bound to the first antibody element;
    the tracer storage site comprises tracer elements comprising a first binder element, a label element and a second antibody element;
    the tracer transport site comprises second binder elements; wherein
    the transport element is configured to be movable towards the tracer transport site and the tracer storage site; and wherein
    the first antibody element has a higher affinity for the analyte than the second antibody element.

The particle may comprise a magnetic nanoparticle.

According to a fourth example aspect of the present invention, there is provided a system for a microfluidic assay, comprising the apparatus of any of the third example aspect of the present invention; and a processor configured to cause carrying out the method of the first and/or second example aspect of the present invention.

The system may further comprise a control element configured to provide the force for moving the transport elements and to handle the fluids in the assay.

The system may further comprise a detection element configured to read out the result of the assay.

According to a fifth example aspect of the present invention, there is provided a computer program comprising computer code for causing performing the method of the first and/or the second example aspect of the present invention, when executed by an apparatus.

According to a sixth example aspect of the present invention, there is provided a non-transitory memory medium comprising the computer program of the fifth example aspect of the present invention.

Different non-binding example aspects and embodiments of the present invention have been illustrated in the foregoing. The embodiments in the foregoing are used merely to explain selected aspects or steps that may be utilized in implementations of the present invention. Some embodiments may be presented only with reference to certain example aspects of the invention. It should be appreciated that corresponding embodiments may apply to other example aspects as well.

BRIEF DESCRIPTION OF THE DRAWINGS

For a more complete understanding of example embodiments of the present invention, reference is now made to the following descriptions taken in connection with the accompanying drawings in which.

DETAILED DESCRIPTION OF THE DRAWINGS

The present invention and its potential advantages are understood by referring to FIGS. 1 through 5 of the drawings. In this document, like reference signs denote like parts or steps.

Figure 1:
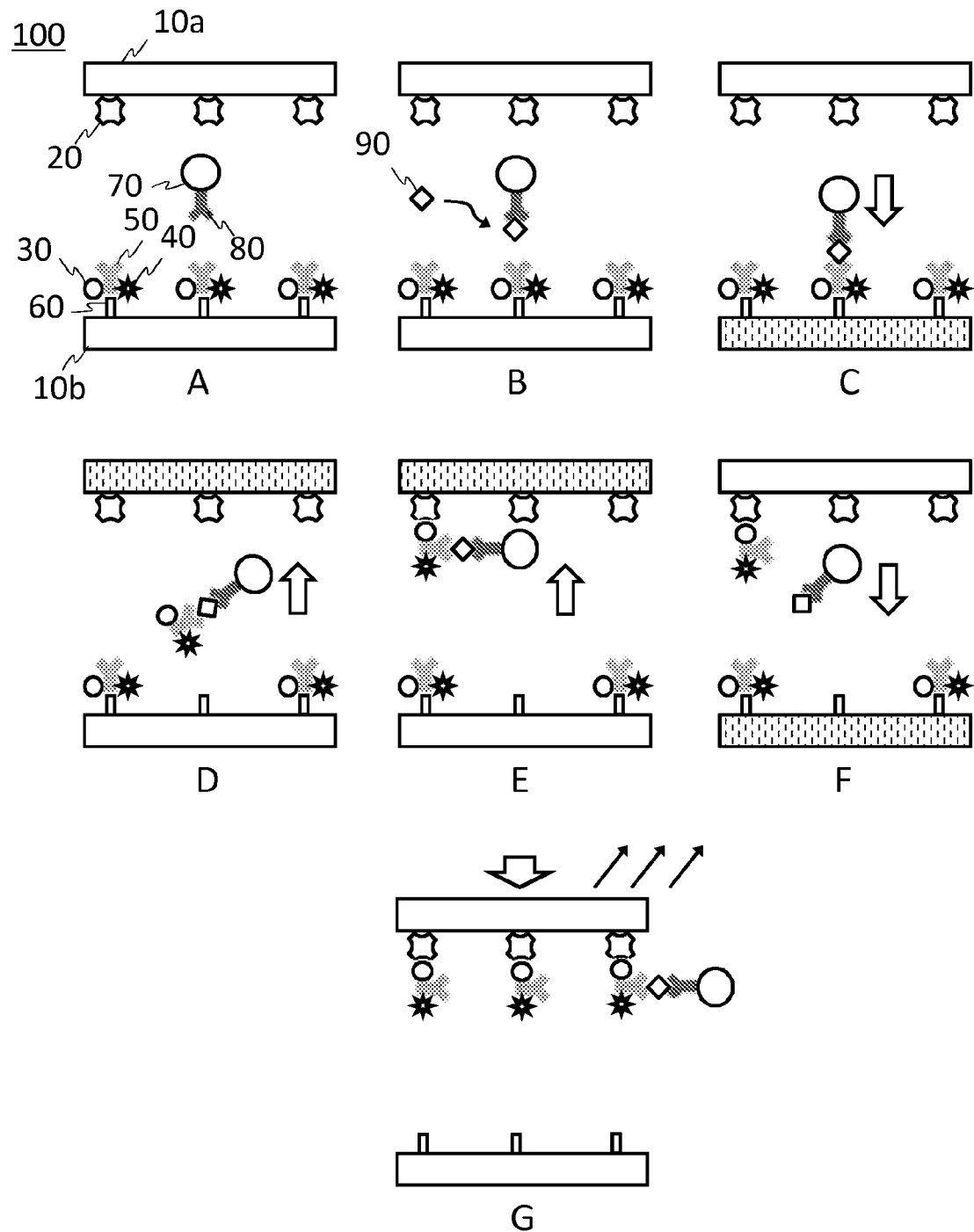
FIG. 1 shows a schematic principle view of an affinity mediated transport amplification and detection according to an embodiment of the invention.

FIG. 1 shows a schematic principle view of an affinity mediated transport amplification and detection according to an embodiment of the invention. FIG. 1 shows the different phases A-G of the affinity mediated transport amplification and detection. Each phase A-G depicts an amount of same components and accordingly, for reasons of intelligibility, a reference sign is only provided for the first appearance of any component.

FIG. 1 shows a microfluidic assay site 100. The assay site comprises a tracer transport site 10a and a tracer storage site 10b. FIG. 1 depicts the transport site 10a and the storage site 10b on opposite sides of the assay site in a vertical direction, i.e. on the top and bottom surface, respectively. In a further embodiment, the transport site 10a and the storage site 10b are positioned on different sides of the assay site 100 in horizontal direction, for example on two opposite side walls. In a still further embodiment, on of the transport site 10a and the storage site 10b is positioned at the top or bottom and the other on a side wall. In a still further embodiment, the transport site 10a and the storage site 10b are positioned on different assay sites on a microfluidic chip, and the fluid is in an embodiment circulated from one to another as needed.

The assay site comprises in the fluidic medium thereof transporter elements. The transporter elements comprise a particle 70. In an embodiment, the particle comprises a microparticle and/or a nanoparticle. In an embodiment, the particles 70 comprise magnetic particles configured to be attracted, i.e. movable, by magnetic force. In a further embodiment, instead of or in addition to the magnetic particle, further particles that are configured to be movable for example electrophoretically or diffusively. The transporter elements further comprise on the surface of the particle 70, a first antibody 80 element configured to have affinity for an analyte to be detected.

The tracer transport site 10a comprises second binder elements 20 on the surface thereof. In an embodiment, the tracer transport site further comprises optical hotspot nanostructures (not shown) configured to localize light used for excitation and comprising the second binder elements 20.

The tracer transport site comprises tracer elements, each tracer element comprising a first binder element 30 configured to have a high affinity for the second binder element 20 in order to form a pair therewith, a label element 40 and a second antibody element 50 configured to have affinity for an analyte to be detected. The second antibody element 50 is configured to have a lower affinity for the analyte to be detected than the first antibody element 80.

The tracer elements are attached to the tracer storage site using an attachment element 60 having a low affinity in such a way that the tracer elements are easily detachable from the tracer storage site 10b. In an embodiment, the attachment element comprises an antibody, a peptide or an aptamer.

The phase A shown in FIG. 1 depicts the situation prior to the introduction of the analyte to be detected, i.e. prior to the affinity mediated transport amplification according to an embodiment of the invention. At phase B fluid comprising the analyte 90 to be detected is introduced into the assay site. In an embodiment, the concentration of the analyte 90 is small, i.e. the fluid comprises only a small amount of analyte 90, i.e. only a few molecules or particles. The analyte 90 comprises a molecule, that can be bound with receptor molecules, such as a protein, a microbe or a virus.

The analyte 90 binds with the first antibody element, that has a high affinity for the analyte and accordingly transport element—analyte pairs are formed at phase B. The following phases C to F comprise phases that are sequentially repeated for the affinity mediated transport amplification according to an embodiment of the invention.

At phase C a force affecting the particles 70 is caused. The direction in which the force attracts the particles 70 is depicted with an arrow in FIG. 1, the direction of the attraction being towards the tracer storage site 10b shown as shaded in FIG. 1. In an embodiment, the force is a magnetic force caused by a magnetic field. In an embodiment, the magnetic field is caused by a magnet being brought to the proximity of the tracer storage site 10b, or the tracer storage site 10b being brought to the proximity of a magnet. In a further embodiment, the magnetic field is caused by an electromagnet at or in proximity of the tracer storage site 10b being turned on. In a further embodiment, instead of or in addition to a magnetic field, for example an electric field for electrophoretic transport is used or diffusive effects are caused.

Due to the effect of the force caused on the particle 70, the transport element moves to the tracer storage site and the analyte 90 bound to the first antibody element 80 is bound to the second antibody element 50 and consequently to the tracer element comprising the second antibody element 50, the first binder element 30 and the label element 40 thus forming a tracer element-analyte-transport element sandwich. In a still further element, instead of a force attracting the particles 70 towards the storage site 10b, the transport element is brought to the transport site by pumping the fluid containing it to the proximity thereof, for example in a situation in which the storage site 10b and the transport site 10a are positioned in separate cuvettes or channels of a microfluidic chip.

At phase D the direction of the force affecting the particles 70 is reversed, so that the transport elements are attracted towards the tracer transport site 10a shown shaded in FIG. 1. The force is generated in the same manner as hereinbefore described with reference to phase C. The attaching element 60 has a low affinity to the second antibody element 50 and accordingly the tracer element detached from the tracer storage site 10b and is pulled towards the tracer transport site 10a together with the analyte 90 and the transport element.

At phase E, the direction of the force remains towards the tracer transport site and consequently, the second binder element 20 and the first binder element 30 having a high affinity towards each other are bound together. Subsequently at phase F the direction of the force affecting the particles 70 is reversed, so that the transport elements are again attracted towards the tracer storage site 10b shown shaded in FIG. 1. The force is generated in the same manner as hereinbefore described with reference to phase C.

Since the affinity of the second antibody element 50 towards the analyte is smaller than that of the first antibody element 80, that between the first 30 and second 20 binder elements and that between the second antibody element 50 and the first binder element, the analyte 90 with the first antibody element 80 and the particle detaches from the tracer element which remains bound to the tracer transport site 10a. Accordingly, the affinity mediated transport amplification has returned to phase C and the phases C to F are repeated predetermined times until enough tracer elements have been bound to the tracer transport site 10a. Should the analyte 90 for some reason detach from the first antibody element during the phases, this error is automatically corrected, as the analyte can be picked up again during subsequent cycles of phases C to F.

At phase G the result of the analyte detection is measured, i.e. phase G comprises a readout phase. The type of readout depends on the type of the label element 40. In an embodiment, the label element 40 comprises a fluorescent label and the readout is carried out by using fluorescent excitation and optical detection of the resulting fluorescence, shown with arrows in FIG. 1. In a further embodiment the readout method is selected from a group of, but not limited thereto, electric methods, for example resistive or capacitive; and optical methods for example using scattering, color changes or raman spectroscopy.

In an embodiment, the affinity mediated transport amplification and detection method according to an embodiment of the invention comprises further phases prior to or after the phases explained hereinbefore. In an embodiment, such phases comprise for example pretreatment and further detection.

Figure 2:
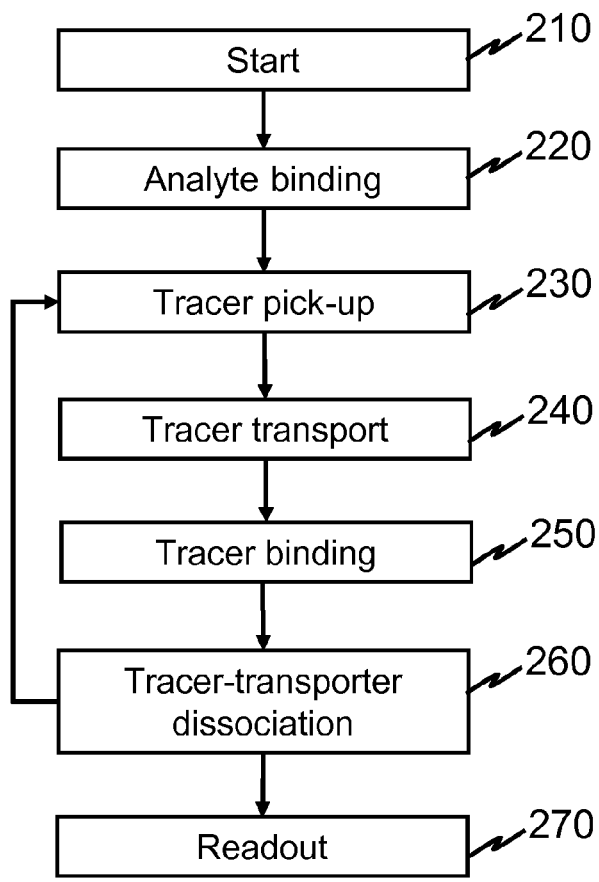
FIG. 2 shows a flow chart of an affinity mediated transport amplification and detection according to an embodiment of the invention.

FIG. 2 shows a flow chart of an affinity mediated transport amplification and detection according to an embodiment of the invention. The steps 210-270 correspond to the phases A-G shown in FIG. 1 and explained hereinbefore with reference thereto.

At step 210 the method is started, i.e. the assay is at its basic state and the fluid containing the analyte 90 is introduced. At step 220 the analyte 90 is bound to the transport element by binding with the first antibody element 80.

At step 230 the analyte 90 is transported together with the transport element towards the tracer storage site 10a as hereinbefore described with reference to FIG. 1 and the analyte 90 binds with the second antibody element 50 of the tracer element, which tracer element is then detached from the tracer storage site 10b at step 240 and transported as hereinbefore described with reference to FIG. 1 together with the transport element and analyte 90 towards the tracer transport site 10a.

At step 250 the first binder element 30 binds with the second binder element 20 of the tracer transport site 10a and subsequently the analyte 90 detaches from the second antibody element and is again transported as hereinbefore described with reference to FIG. 1 with the transport element towards the tracer storage site 10b. The steps 230 to 260 are repeated a predetermined number of times in a cycle to ensure the amplification. The number of repetitions, i.e. the number of cycles is dependent on the analyte and the concentration thereof and on the other elements used.

Figure 3:
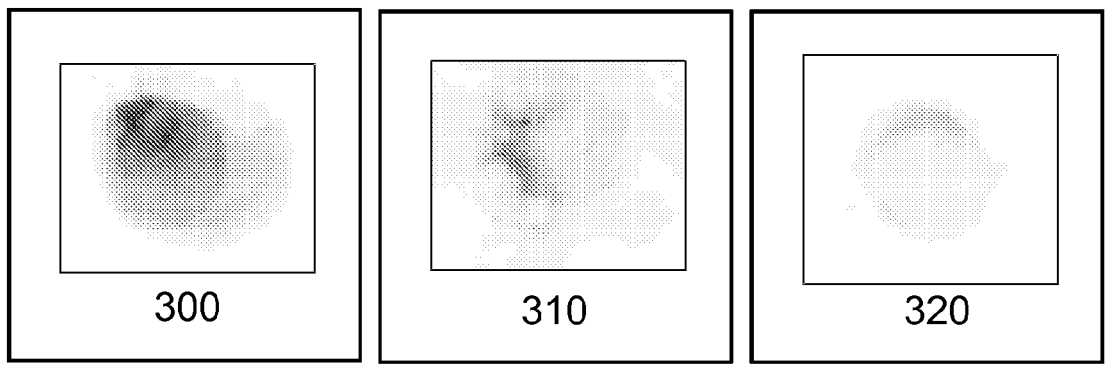
FIG. 3 shows example readout results of an affinity mediated transport amplification and detection according to an embodiment of the invention.

FIG. 3 shows example readout results of an affinity mediated transport amplification and detection according to an embodiment of the invention. In the example, the analyte 90 comprised C reactive protein (CRP). The second antibody element 50 comprised a CRP antibody having an association constant $K_A$ of $1,4 \times 10^{10}$ 1/M. The first antibody element 80 comprised a CRP antibody having an association constant $K_A$ of $3,9 \times 10^{10}$ 1/M. The attachment element 60 comprises saccharide, the second binder element 20 comprised avidin, the first binder element comprised biotin and the label element comprised Alexa AF647 Fluorescent dye. The particles 70 comprised magnetic nanoparticles and the magnetic field was generated by bringing a permanent magnet into proximity of the tracer storage site 10b or the tracer transport site 10a. The method was carried out in a microfluidic chip with 10 amplification cycles, i.e. the phases C-F of FIG. 1 were carried out 10 times, with fluorescent excitation and readout. The left side image 300 of FIG. 3 shows a positive detection of analyte CRP after 10 cycles. The middle image 310 of FIG. 3 shows a first negative control with influence of unspecific binding showing in the image, i.e. the 10 cycles were carried out without the analyte CRP. The right side image 320 of FIG. 3 shows a second negative control with influence of diffusive tracer transport, i.e. the readout was carried out without the amplification cycles.

Figure 4:
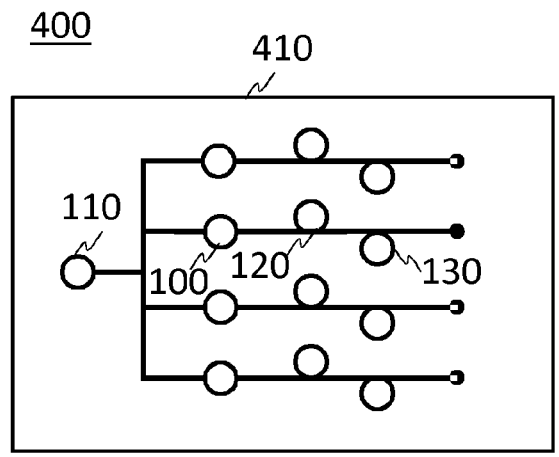
FIG. 4 shows a schematic principle view of an apparatus for affinity mediated transport amplification and detection according to an embodiment of the invention.

FIG. 4 shows a schematic principle view of an apparatus 400 for affinity mediated transport amplification and detection according to an embodiment of the invention. In an embodiment, the apparatus 400 comprises a microfluidic chip 410 as depicted schematically. In a further embodiment, the apparatus comprises a further structure in which the necessary fluidic structures are provided.

FIG. 4 shows the microfluidic chip 410 comprising fluid channels depicted with black lines. Furthermore, FIG. 4 shows assay sites, or cuvettes depicted as rings. FIG. 4 shows several branches of fluidic channels for carrying out operations. In FIG. 4, each channel has the same structure and accordingly, the reference signs are provided for a single channel only for reasons of intelligibility.

The microfluidic chip 410 comprises an input port 110 configured to allow insertion of fluids containing the transport elements of the affinity mediated transport amplification according to an embodiment of the invention into the chip and to allow the fluid containing an analyte to be inserted into the chip. Although a single input port 110 is shown, in an embodiment the microfluidic chip comprises several.

The microfluidic chip 410 further comprises assay sites 100 configured for carrying out the affinity mediated transport amplification and detection as hereinbefore described. The assay sites 100 comprise the tracer transport site 10a and tracer storage site 10b as hereinbefore described. The microfluidic chip further comprises, in an embodiment, an element (not shown) configured to provide the force for attracting the transport elements as hereinbefore described, such as a magnet or electric field generator. In a still further embodiment, the tracer transport site 10a and the tracer storage site 10b are situated in separate assay elements and fluidly connected, in which embodiment, the microfluidic chip comprises for example a pump (not shown) for moving fluid therebetween. It is to be noted that the microfluidic structures used are per se known to a skilled person.

In an embodiment, the microfluidic chip comprises further assay sites 120,130. Even though two further assay sites have been depicted, the microfluidic chip may comprise one or more further assay sites. The further assay sites are in an embodiment configured e.g. for further tests.

Figure 5:
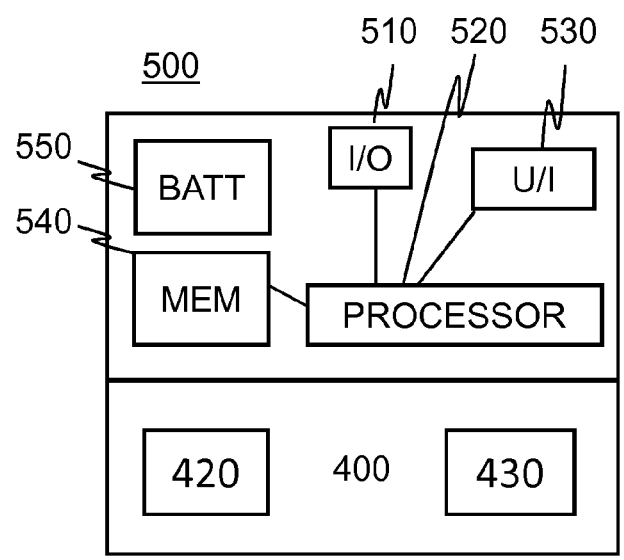
FIG. 5 shows a block view of a system for affinity mediated transport amplification and detection according to an embodiment of the invention.

FIG. 5 shows FIG. 5 shows a block view of a system for affinity mediated transport amplification and detection according to an embodiment of the invention. The system 500 comprises an apparatus 400 for affinity mediated transport amplification and detection according to an embodiment of the invention as hereinbefore described. The apparatus 400 comprises or is connected with a control element 420 comprising the elements, for example magnets, for providing the force needed for attracting the transporter elements as hereinbefore described and fluid handling elements. The apparatus 400 further comprises or is connected with a detection element 430 for reading the result of the affinity mediated transport amplification assay as hereinbefore described. In an embodiment, the system 500 comprises more than one apparatus 400 according to an embodiment of the invention.

The system 700 further comprises electronics configured to control the operations of the system and apparatus, to carry out calculations and to cause carrying out the steps of the method according to the invention. The system 500, in an embodiment, comprises a memory 540 and a processor 520. The processor 520 is, in an embodiment, configured to control the apparatus 400 and to cause storing the data into the memory 540. The processor 520 is further configured to cause controlling of the operation of the system 500 and the apparatus 400 using a non-transitory computer program code stored in the memory 540.

In a further embodiment, the system 500 comprises a communication unit 510 comprising, for example, a local area network (LAN) port; a wireless local area network (WLAN) unit; Bluetooth unit; cellular data communication unit; near field communication unit or satellite data communication unit. The system 500 further comprises a power source, such as a battery 550 or a connection to external power.

In a further embodiment the system 500 comprises a user interface unit 530 comprising for example a display or a touch display for showing the measurement result. In a still further embodiment, the system 500 comprises, or is comprised in, a personal electronic device such as a laptop computer, a tablet computer or a personal computer and configured to co-operate with the apparatus 400. In an embodiment, the system 500 is comprised in a larger entity, such as a control system of a laboratory or field test unit.

Without in any way limiting the scope, interpretation, or application of the claims appearing below, a technical effect of one or more of the example embodiments disclosed herein is the provision of an amplification without amplification of background noise. Another technical effect of one or more of the example embodiments disclosed herein is robust amplification with in-built error correction. Another technical effect of one or more of the example embodiments disclosed herein is the provision of a detection of very small analyte concentrations, even single molecules.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the foregoing describes example embodiments of the invention, these descriptions should not be viewed in a limiting sense. Rather, there are several variations and modifications which may be made without departing from the scope of the present invention as defined in the appended claims.

The invention claimed is:

1. An apparatus for a microfluidic assay for analyte detection, the apparatus comprising:
 a microfluidic chip including at least one input port for introducing a fluid containing an analyte, and at least one assay site, the at least one assay site including transport elements, a tracer transport site, and a tracer storage site; wherein:
 a transport element of the transport elements includes a particle and a first antibody element, the first antibody element configured to be bound to the analyte;
 the tracer storage site includes tracer elements, each of the tracer elements including a second antibody element bound to a first binder element and to a label element;
 the tracer transport site includes second binder elements, each second binder element configured to bind with a first binder element of one of the tracer elements; wherein:
 the transport element is configured to be movable towards the tracer transport site and the tracer storage site; and
 the first antibody element has a first affinity for the analyte and the second antibody has a second affinity for the analyte, the first affinity being higher than the second affinity;
 the second antibody element having a third affinity for the tracer storage site, the second affinity being higher than the third affinity; and
 the second affinity being lower than a fourth affinity between the first and second binder elements and lower than a fifth affinity between the second antibody element and the first binder element.

2. The apparatus of claim 1, wherein the particle comprises a magnetic nanoparticle.

3. A system for a microfluidic assay for analyte detection, the system comprising:
a microfluidic chip, comprising at least one input port for introducing a fluid containing an analyte, and at least one assay site, the assay site comprising transport elements, a tracer transport site, and a tracer storage site; wherein
a transport element of the transport elements comprises a particle and a first antibody element, the first antibody element configured to be bound to the analyte;
the tracer storage site comprises tracer elements comprising a second antibody element bound to a first binder element and to a label element;
the tracer transport site comprises second binder elements for binding with a first binder element; wherein:
the transport element is configured to be movable towards the tracer transport site or towards the tracer storage site; and
the first antibody element has a higher affinity for the analyte than the second antibody element has for the analyte;
the second antibody element has a higher affinity for the analyte than for the tracer storage site; and
the affinity of the second antibody element towards the analyte is lower than an affinity between the first and second binder elements and lower than an affinity between the second antibody element and the first binder element; and
a processor operably associated with the microfluidic chip.

4. The system of claim 3 further comprising a control element configured to provide force for moving the transport elements and for handling the fluid in the assay.

5. The system of claim 3, further comprising a detection element configured to read out a result of the assay.

6. The system of claim 3, wherein the particle includes a magnetic nanoparticle.

7. The system of claim 3, wherein the tracer elements are selectively attached to the tracer storage site with attachment elements.

8. The apparatus of claim 1, wherein the tracer elements are selectively attached to the tracer storage site with attachment elements.

9. An apparatus for a microfluidic assay for analyte detection, the apparatus comprising:
a microfluidic chip including at least one input port and at least one assay site, the at least one input port configured to introduce a fluid containing an analyte, the at least one assay site including at least one transport element, a tracer storage site, and a tracer transport site, the at least one transport element including a particle and a first antibody element, the first antibody element configured to be bound to the analyte, the at least one transport element being selectively movable between the tracer transport site and the tracer storage site, the tracer storage site including at least one tracer element, the at least one tracer element including a second antibody element bound to a first binder element and to a label element, the tracer transport site including a second binder element, the second binder element configured to bind with the first binder element of the least one tracer element, wherein:
the first antibody element has a higher affinity for the analyte than the second antibody element has for the analyte;
the second antibody element has a higher affinity for the analyte than for the tracer storage site; and
the affinity of the second antibody element towards the analyte is lower than an affinity between the first and second binder elements and lower than an affinity between the second antibody element and the first binder element.

10. The apparatus of claim 9, wherein the particle includes a magnetic nanoparticle.

11. The apparatus of claim 9, wherein the at least one tracer element is selectively attached to the tracer storage site.

* * * * *